(12) United States Patent
Rosero et al.

(10) Patent No.: US 11,246,486 B2
(45) Date of Patent: Feb. 15, 2022

(54) INTRA-BODY COMMUNICATION METHOD FOR IMPLANTED AND NON-IMPLANTED BIOSENSORS OR DEVICES

(71) Applicant: Efferent Labs, Inc., Buffalo, NY (US)

(72) Inventors: Spencer Z. Rosero, Pittsford, NY (US); William K. Rader, Huger, SC (US)

(73) Assignee: EFFERENT LABS, INC., Buffalo, NY (US)

(*) Notice: Subject to any disclaimer, the term of this patent is extended or adjusted under 35 U.S.C. 154(b) by 189 days.

(21) Appl. No.: 15/424,734

(22) Filed: Feb. 3, 2017

(65) Prior Publication Data
US 2017/0231498 A1 Aug. 17, 2017

Related U.S. Application Data

(60) Provisional application No. 62/291,763, filed on Feb. 5, 2016.

(51) Int. Cl.
*A61B 5/00* (2006.01)
*A61B 5/0205* (2006.01)
(Continued)

(52) U.S. Cl.
CPC ............ *A61B 5/0031* (2013.01); *A61B 5/002* (2013.01); *A61B 5/0004* (2013.01); *A61B 5/0017* (2013.01); *A61B 5/0028* (2013.01); *A61B 5/0205* (2013.01); *A61B 5/02055* (2013.01); *A61B 5/1473* (2013.01); *A61B 5/14532* (2013.01); *A61B 5/283* (2021.01);
(Continued)

(58) Field of Classification Search
None
See application file for complete search history.

(56) References Cited

U.S. PATENT DOCUMENTS

| 2004/0015211 A1 | 1/2004 | Nurmikko et al. |
| 2004/0152953 A1 | 8/2004 | Goedeke |

(Continued)

FOREIGN PATENT DOCUMENTS

| JP | 2002509460 A | 3/2002 |
| JP | 2005511184 A | 4/2005 |

(Continued)

OTHER PUBLICATIONS

Extended European Search Report dated Jul. 24, 2019, European Application No. 17748320.0, pp. 1-12.

(Continued)

*Primary Examiner* — Ankit D Tejani
(74) *Attorney, Agent, or Firm* — Biopharma Law Group, PLLC

(57) ABSTRACT

An intra-body communication system for monitoring physiological changes in a patient is provided. The system can include a first device implanted into a patient's body; a second device spaced apart from the first device; and a receiver for detecting and/or decoding the signals to monitor physiological changes in the patient. The first device and second device are capable of engaging in a two-way communication through transmission of one or more signals through at least a portion of the patient's body between the first device and the second device. In one embodiment, the signal may be an optical signal.

11 Claims, 3 Drawing Sheets

(51) Int. Cl.
  *A61B 5/283* (2021.01)
  *A61B 5/145* (2006.01)
  *A61B 5/1473* (2006.01)
  *H04B 10/80* (2013.01)
  *H04B 13/00* (2006.01)
  *A61B 5/024* (2006.01)
  *A61B 5/0215* (2006.01)

(52) U.S. Cl.
  CPC .......... *A61B 5/4836* (2013.01); *A61B 5/686* (2013.01); *A61B 5/7271* (2013.01); *H04B 10/80* (2013.01); *H04B 13/005* (2013.01); *A61B 5/0006* (2013.01); *A61B 5/0008* (2013.01); *A61B 5/0024* (2013.01); *A61B 5/024* (2013.01); *A61B 5/0215* (2013.01); *A61B 5/02444* (2013.01)

(56) References Cited

U.S. PATENT DOCUMENTS

| | | | |
|---|---|---|---|
| 2005/0245798 A1 | 11/2005 | Yamaguchi et al. | |
| 2008/0046037 A1 | 2/2008 | Haubrich et al. | |
| 2012/0041289 A1* | 2/2012 | Rosero | A61N 1/05 600/310 |
| 2012/0238839 A1* | 9/2012 | Hyde | A61B 5/14507 600/310 |
| 2013/0027186 A1 | 1/2013 | Cinbis et al. | |
| 2014/0094674 A1 | 4/2014 | Nurmikko et al. | |

FOREIGN PATENT DOCUMENTS

| | | |
|---|---|---|
| JP | 2005230521 A | 9/2005 |
| JP | 2006519052 A | 8/2006 |
| WO | 9831276 A1 | 7/1998 |
| WO | 03049592 A2 | 6/2003 |
| WO | 2004066834 A1 | 8/2004 |

OTHER PUBLICATIONS

International Search Report and Written Opinion dated Apr. 17, 2017, International Application No. PCT/2017/016601, pp. 1-7.
Japanese Office Action dated Jan. 5, 2021, Japanese Application No. 2018-540120, pp. 1-15 (Includes English Launguage Translation of Office Action).
Abidin, S. et al., "Infra Red Radiation Detection using Passive Infrared Sensor," International Journal of Computer Applications (0975-8887) 152(5):35-38, Oct. 2016.
Second Office Action dated Aug. 26, 2021 in Chinese Patent Application No. 201780021485.4, pp. 1-24 (Includes English Translation).
Baohua Wang et al., "Advanced Course in Biomedical Electronics," Southwest University Press, vol. 1, Mar. 2001, pp. 1-14 (Includes English Translation).

* cited by examiner

INTRA-BODY COMMUNICATION METHOD FOR IMPLANTED AND NON-IMPLANTED BIOSENSORS OR DEVICES

FIELD OF THE INVENTION

The present invention relates to implantable sensors suitable for monitoring physiological changes within the body.

BACKGROUND

Generally, wireless communication provides an advantage over lead based systems but also introduces a new technical problem: electromagnetic interference. Wireless systems based on RF are inherently susceptible to environment EMI (electromagnetic interference) and have significant power requirements that limit implantable technology.

The potential problems that patients can experience due to communication interruptions in any implantable cardiac device whether wireless or lead based, include inappropriate shock therapy, unintended inhibition of pacing due to over sensing, commanded therapy signaling may not be received and acted upon, and early battery depletion because of need to repeat transmission or increase power of transmission. The potential issue of wireless communication affecting an unintended patient in the same vicinity as the patient with the device of interest at that time needs to be addressed.

Recent advances allowing the verification and security of data being transmitted to the targeted device have minimized the concern in this area. Pacemaker/ICD programmers have addressed the problem in systems that clinicians use to interrogate pacemakers in the office. If one tries to interrogate a different device when the previous patient's software interface is active, the device does not allow it because it recognizes a different Controller ID during communication. A new link is then required. This encoding can be done at the micro level and provides the safeguards needed. The main technical challenges will involve securing accurate transmission of data between modules including implantable cell based sensors.

Thus, there is a need for a novel system that utilizes at least two (2) and possibly three (3) different media for communication within a single implantable biosensor system. While the use of RF and ultrasonic communication within or around the body is well established, the invention of the present application uses optical emission that specifically uses the body and its tissues as the medium through which to communicate.

SUMMARY

There is a need for improved intra-body communication systems and methods for monitoring physiological changes in a patient. The present invention is directed toward further solutions to address this need, in addition to having other desirable characteristics.

In accordance with an example embodiment of the present invention, an intra-body communication system for monitoring physiological changes in a patient is disclosed. The system can include a first device implanted into a patient's body; a second device spaced apart from the first device; and a receiver for detecting and/or decoding the signals to monitor physiological changes in the patient. The first device and second device are capable of engaging in a two-way communication through transmission of one or more signals through at least a portion of the patient's body between the first device and the second device.

In accordance with aspects of the present invention, the first device can have a biologic component.

In accordance with yet further aspects of the present invention, the biologic component can have a cell layer having cells from the target site pre-positioned on or in the device prior to implantation.

In accordance with yet further aspects of the present invention, the pre-positioned cells can be adapted to respond to a physiological signal from a patient.

In accordance with yet further aspects of the present invention, the first device can further include an electronic component.

In accordance with yet further aspects of the present invention, the electronic component can have at least one sensor and at least one electrode contacting said biologic component.

In accordance with yet further aspects of the present invention, the second device can be implanted inside the patient's body.

In accordance with yet further aspects of the present invention, the second device can be external to the patient's body.

In accordance with yet further aspects of the present invention, the two-way communication includes transmitting and receiving optical signals.

In accordance with yet further aspects of the present invention, the optical signal is selected from the group consisting of infrared light, visible light, and ultraviolet light.

In accordance with yet further aspects of the present invention, the signal can include infrared light, visible light, ultraviolet light, radio waves, microwaves, X-rays, gamma rays, and ultrasonic signals or combinations thereof.

In accordance with yet further aspects of the present invention, the signals can be transmitted with a wavelength frequency in a range of approximately $1 \times 10^{-8}$ to $1 \times 10^{-1}$ Hz.

In accordance with yet further aspects of the present invention, the signals can travel through the body with minimal interference from the surrounding tissues or organs.

In accordance with yet further aspects of the present invention, the signals can measure blood pressure, ECG, heart rate, body temperature, glucose levels, gene and protein changes, local cellular changes that reflect systemic disease or change in health status or combinations thereof.

In accordance with yet further aspects of the present invention, the receiver can compare the signal to a reference signal to diagnose a disease or condition.

In accordance with yet further aspects of the present invention, the receiver can decode the signal to trigger an event.

In accordance with yet further aspects of the present invention, the event may include adjusting the patient's medical treatment.

In accordance with an example embodiment of the present invention, a method for monitoring physiological changes in a patient is provided. The method can include the steps of: providing an intra-body communication system; transmitting one or more signals through at least a portion of the patient's body between the first device and the second device; and providing a receiver for detecting and/or decoding the signals to monitor physiological changes in the patient. The intra-body communication system can include a first device implanted into a patient's body; a second device spaced apart from the first device; and a receiver for detecting and/or decoding the signals to monitor physiological changes in the patient. The first device and second device are capable of engaging in a two-way communication through transmission of one of more signals through at least a portion of the patient's body between the first device and the second device.

In accordance with an example embodiment of the present invention, a method of diagnosing a patient is provided. The method can include the steps of: providing an intra-body communication system; transmitting one or more signals through at least a portion of the patient's body between the first device and the second device; detecting and/or decoding the one or more signals to monitor physiological changes in the patient; and comparing the one or more signals in the patient to a reference signal to diagnose a disease or condition. The intra-body communication system can include a first device implanted into a patient's body; a second device spaced apart from the first device; and a receiver for detecting and/or decoding the signals to monitor physiological changes in the patient. The first device and second device are capable of engaging in a two-way communication through transmission of one of more signals through at least a portion of the patient's body between the first device and the second device.

In accordance with an example embodiment of the present invention, a method of treating a patient is provided. The method can include the steps of: providing an intra-body communication system; transmitting one or more signals through at least a portion of the patient's body between a first device and a second device; detecting and/or decoding the signal(s) to monitor physiological changes in the patient; reviewing and/or analyzing the signal(s); and treating the patient based on the review and/or analysis of the signal(s). The intra-body communication system can include the first device implanted into the patient's body; the second device spaced apart from the first device; and a receiver for detecting and/or decoding the signal(s) to monitor physiological changes in the patient. The first device and second device are capable of engaging in a two-way communication through transmission of one of more signals through at least a portion of the patient's body between the first device and the second device.

BRIEF DESCRIPTION OF THE FIGURES

These and other characteristics of the present invention will be more fully understood by reference to the following detailed description in conjunction with the attached drawings, in which.

DETAILED DESCRIPTION

An illustrative embodiment of the present invention relates to an intra-body communication system suitable for monitoring physiological changes within the body.

Figure 1:
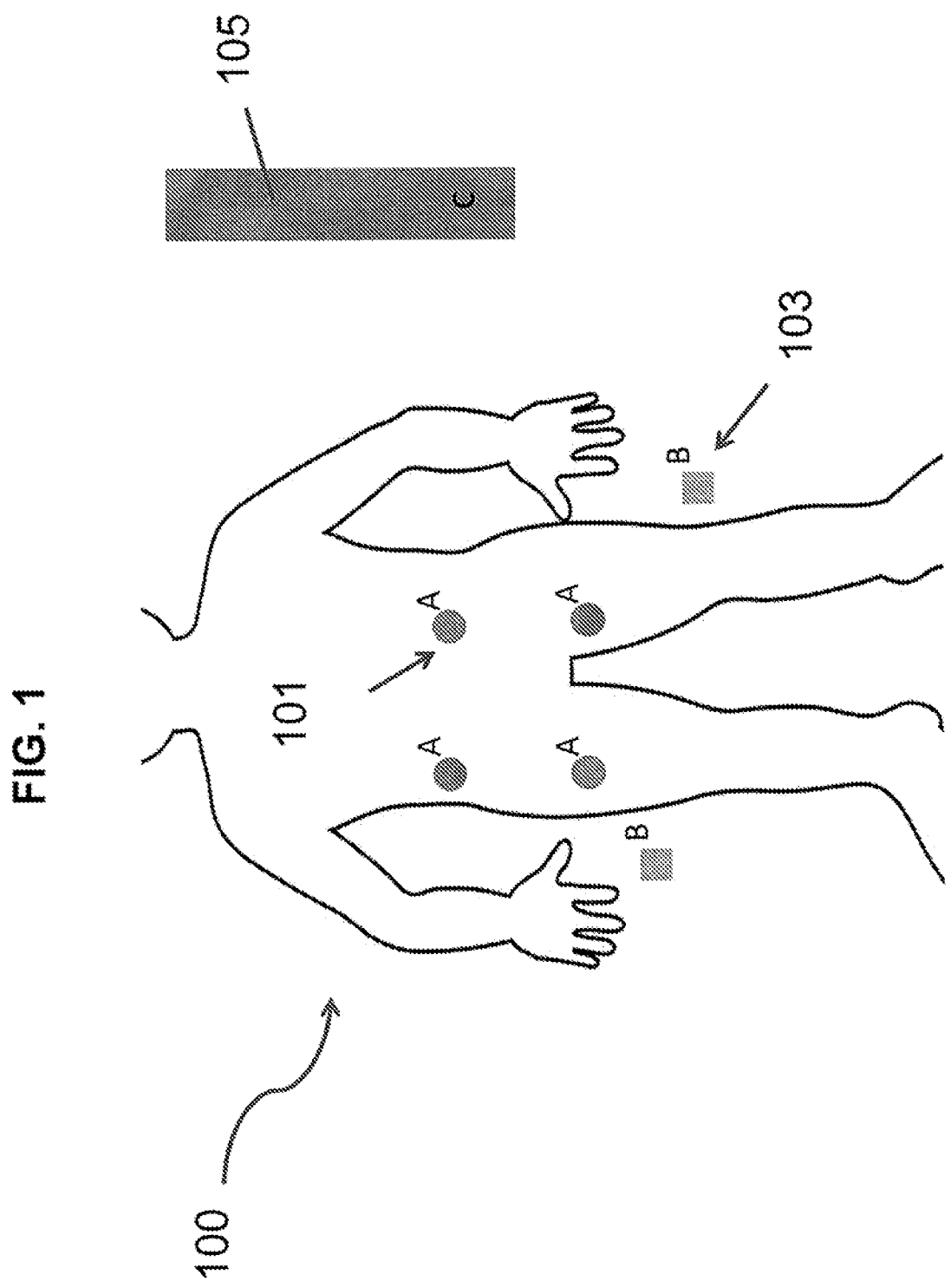
FIG. 1 is a drawing of an intra-body communication (IBC) system in accordance with an embodiment of the present invention.
Figure 2:
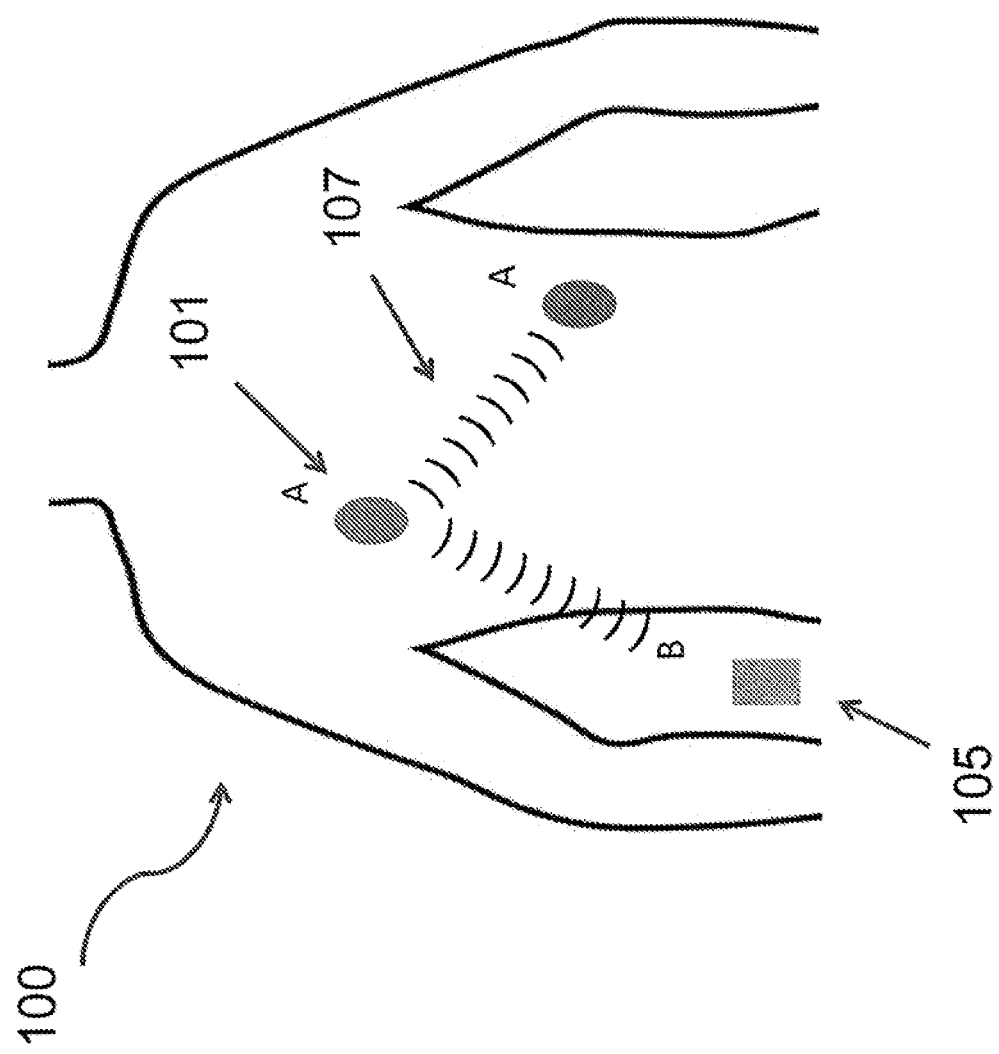
FIG. 2 is a drawing of an intra-body communication (IBC) system in accordance with an embodiment of the present invention.
Figure 3:
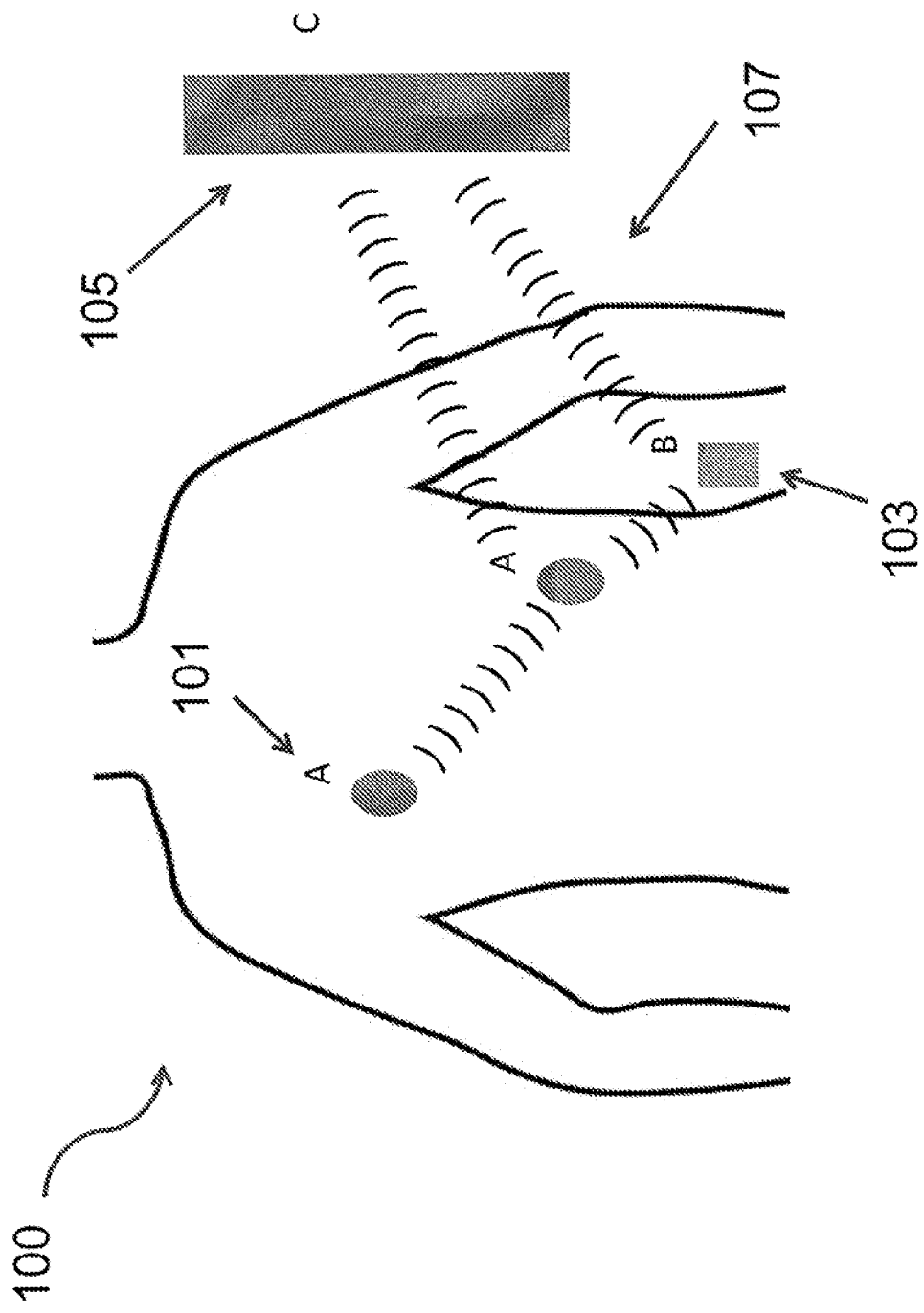
FIG. 3 is a drawing of an intra-body communication (IBC) system in accordance with an embodiment of the present invention.

FIG. 1 through FIG. 3, wherein like parts are designated by like reference numerals throughout, illustrate an example embodiment or embodiments of an intra-body communication system suitable for monitoring physiological changes within the body, according to the present invention. Although the present invention will be described with reference to the example embodiment or embodiments illustrated in the figures, it should be understood that many alternative forms can embody the present invention. One of skill in the art will additionally appreciate different ways to alter the parameters of the embodiment(s) disclosed, such as the size, shape, or type of elements or materials, in a manner still in keeping with the spirit and scope of the present invention.

As FIG. 1 illustrates, embodiments of an intra-body communication system 100 may comprise implantable devices for monitoring physiological changes within the body. As used herein, "intra-body communication" may refer to internal communication within a single mammalian body. However, sensors and components can be positioned internally or externally to the individual. In one embodiment, the intra-body communication system 100 may comprise a first device 101 that produces a signal and a second device 103 spaced apart from the first device 101 for receiving the signal. In one embodiment, the direction of the signals is reversed. In one embodiment, both the first device 101 and the second device 103 are situated within the body. In another embodiment, only one of the components is external to the individual while the other is internal in the body. For instance, the first device 101 is internal in the body while the second device 103 is external to the body. In another embodiment, there may be any number devices implanted within the body or situated external to the body.

In an embodiment, the first device 101 may include a biologic component and an electronic component. In an embodiment, the biologic component may include a cell layer having cells from the target site pre-positioned on or in the device prior to implantation. The pre-positioned cells may be adapted to respond to a physiological signal from a patient. In an embodiment, the electronic component may include at least one sensor and at least one electrode contacting the biologic component. The first device 101 may be the same or substantially the same as that described in U.S. Pat. Nos. 8,024,020; 8,849,416; 8,938,300 and U.S. patent application Ser. No. 13/212,804 all of which are hereby incorporated by reference.

In an embodiment, the second device 103 may be the same or substantially the same as the first device 101. In another embodiment, the second device 103 may be different from the first device 101. For instance, the second device 103 may a pace maker, a glucose monitor pump, an insulin pump, a neurostimulator, a defibrillator or any other medical device that can be implanted within or carried on a person.

As shown in FIG. 2, the first device 101 and second device 103 are capable of engaging in a two-way communication through transmission of one of more signals 107 through at least a portion of the patient's body between the first device 101 and the second device 103. In an embodiment, the two-way communication includes transmitting and receiving signals. In an embodiment, the signals may be optical signals or light signals. As used herein, "optical signals" may refer to infrared light, visible light, and ultraviolet light. In accordance with an embodiment of the present invention, the signals may be infrared light. In accordance with an embodiment of the present invention, the signals may be visible light. In accordance with an embodiment of the present invention, the signals may be ultraviolet light. In accordance with an embodiment of the present invention, the signals may include infrared light, visible light, ultraviolet light, electromagnetic radiation, radio waves, microwaves, X-rays, gamma rays, ultrasonic signals or combinations thereof. It should be appreciated that other signals known in the art may also be included.

In an embodiment, the signals 107, e.g., optical signals, may travel through the body with minimal interference from the surrounding tissues or organs. For instance, the signals 107, e.g., optical signals, may travel through muscles, organs such as lungs and the heart, bone, cartilage, or any other tissues in the body while experiencing minimal interference and/or loss in wavelength frequency. In an embodiment, it is expected that the loss in wavelength frequency will be less than 10%, less than 9%, less than 8%, less than 7%, less than 6%, less than 5%, less than 4%, less than 3%, less than 2%, or less than 1%. It should be appreciated that the amount of loss can vary based on a number of factors. For instance, the amount of loss can depend on the type of signal and/or the type of wavelength selected. In addition, the amount of loss may depend on the amount of absorption, diffusion and/or scatter. It should be appreciated by one skilled in the art, however, that the amount of loss will be minimal and will not impact the operation of the invention of the present application.

In some embodiments, the signal is encoded using frequency and/or amplitude modulation. In this way, the signals 107, e.g., optical signals, may carry data such as blood pressure, heart rate, ECG, body temperature, glucose levels, gene and protein changes, local cellular changes that reflect systemic disease or change in health status or other body parameters to receiver 105. In an embodiment, the optical signals may have a wavelength frequency in a range of approximately $1 \times 10^{-8}$ to $1 \times 10^{-1}$ Hz. Of course, it should be appreciated to anyone skilled in the art that the wavelengths may vary.

After traveling through the body, the signal 107 can be transmitted to the receiver 105, as shown in FIG. 3, which then detects the signal 107. In addition, receiver 105 may decode or demodulate the signal 107 to receive the data encoded within the signal 107 and may compare the signal 107 to a reference signal to diagnose the disease or condition. In response to the detected signal 107, receiver 105 may initiate an action. The action can include adjusting the patient's medical treatment (e.g. drug delivery), activate an alarm, send information to the physician, etc.

Accordingly, it is envisioned that the disclosed intra-body communication system 100 may be used in numerous applications. In one embodiment, the intra-body communication system 100 may be used for drug release applications. For example, an internal drug dispensing device may be implanted within a patient. The receiver 105 may be coupled to the drug dispensing device. In response to a signal 107, the receiver 105 may instruct the drug dispensing device to release drugs into the body. Sensors may then detect the effectiveness of the drug and allow the user to trigger another dose release. Such systems may allow for patient targeted treatment. This may be particularly useful in chronically ill patients, such as diabetic patients or patients undergoing cancer treatment.

In another application, the intra-body communication system 100 may be used in health monitoring. Similar to the above application, the receiver 105 may detect and decode the signal 107 and may store data on a storage medium such as a flash card, hard drive, or other devices known to those of skill in the art and/or send the data to a base station, such as a computer, a smart phone, or cell phone. Depending on the complexity of the system setup the information may be forwarded directly to a physician's office or nurse's station, first responders, or other qualified personnel who may then review the data and access the best possible treatment path forward.

In a further application, embodiments of the disclosed intra-body communication system 100 could be used to diagnose medical conditions. Currently, a health care professional may be able to diagnose conditions and diseases only after reviewing and analyzing data such as the results of blood work, x-ray, computed tomography or magnetic resonance imaging, etc. Without being limited to theory, it is believed that conditions or diseases may have distorted signal 107. In a healthy individual, the signal 107 may be transmitted differently than in an unhealthy individual. Using an embodiment of the disclosed system, differences in the signal 107 or rate of transmission may alert a health care professional of a possible injury, disease or condition.

To further illustrate various illustrative embodiments of the present invention, the following examples are provided.

We are proposing an intra-body communication system that utilizes at least two (2) and as needed three (3) different media for communication within a single implantable biosensor system. The system uses optical emission that specifically uses the body and its tissues as the medium through which to communicate.

Communication may be on any wavelength appropriate for the anatomical distance and substances/tissues surrounding the two points of communication.

This approach will focus on optical (infrared) in a synchronized fashion to minimize potential gaps in information during transmission since one mode can provide the necessary information at that time. The method of communication that is used in phase I is that all sensors, including cell based implanted biosensors, have their own unique address and all sensors are listening for commands. A host controller sends out a command with an embedded address to all sensors. The sensor with the correct address will respond to the command and then send out an acknowledgement. All other sensors ignore the command and wait for another command to be sent.

There is minimal information in the literature about using non-RF based methods for communication between modules that are implanted in the body. In Phase I, we will explore various options for wireless communication including infrared, ultrasound, and RF. Important considerations during Phase I include ease of use in prototype development, cost, minimal power requirements, and the need to use the data for advanced development of RF, light based, and/or acoustic communication specifically for use in the proof of concept prototype.

INFRARED: While all wireless serial communications methods have their own advantages and disadvantages, infrared communication (IRC) offers a number of advantages in this application. IRC hardware has potentially the least number of components. They include emitters, detectors, amplifiers and pulse code modulators/demodulators (PCMD). These components can be small and require less support components.

Technology exists to detect and transmit light within the infrared spectrum. All objects that have a temperature greater than that of absolute zero (−273.16 degrees C.) emit electromagnetic energy. The spectrum at which energy is emitted is directly related to the temperature of the object. The human body emits electromagnetic radiation at 9.3 uM wavelength. The infrared range is defined as electromagnetic energy with a wavelength of 0.7 uM-1000 uM. Since the body itself emits infrared light, it poses a problem for an infrared device to isolate true signals versus noise. The same light is also altered as it passes through human tissue, specifically as the light is transmitted and reflected between various cell layers and organs. This change in medium, akin to light passing from air to liquid, alters some of the characteristics of the particular signal such as the wavelength and velocity but not the frequency of the wave pattern. This fact allows for relatively preserved signaling using infrared within the human body.

A significant challenge is that of diode power and sensor capabilities, both of which are directly related to the distance and medium through which the infrared signal must travel. For example, an infrared signal that needs to be carried from one part of the heart to another would likely be hampered by the heart muscle itself, the blood/tissue interface within the cardiac chamber, as well as the surrounding tissue it may need to penetrate. However, infrared light can be used in a reflective manner within the body and provides advantages. One needs to consider the ability of light to reflect off tissue surfaces and use this fact to design a system that combines both properties of penetration and reflection capabilities within the media (body tissue). In this case, a module placed on the epicardial right ventricle would communicate to the module implanted in the left ventricle by transmitting the signal and allowing it to be reflected and absorbed by surrounding tissue. The sensors at the designated receiving site can decode the information. Specific designs that reflect light to target regions are available and this can be used in the construction of site specific transmission and receiving modules.

The advantages offered by the body as the primary medium in the proposed technology includes a very stable and narrow temperature range in the human, limited distances, and relatively consistent anatomy between individuals allowing for modeling of various tissue: tissue interfaces. Environmental noise needs to be considered as well. Since the body can absorb infrared as well as most wavelengths of electromagnetic radiation, one must consider the potential interference posed to an implanted infrared system when the patient is exposed to various environments including fluorescent lighting, bright summer sun, etc.

Design Challenges: IRC can communicate over several meters in free air. In the body, infrared light will be greatly diffused and attenuated. The communication distance within the body will be approximately 10 inches. The body's tissues attenuate some wavelengths of infrared light less than others. Experiments will determine the most effective wavelength of infrared source. Powerful and efficient infrared sources are available. Infrared sources are generally unidirectional. The infrared source light, though attenuated, will be diffused and refracted by the body's tissues. This will, in effect, make the source omnidirectional. The detector will be required to be sensitive to pick up the infrared source light. The body's tissues will provide a natural ambient light filter reducing noise. Additionally, infrared systems frequently operate at 95 kHz and 250 kHz, 300 kHz, 2.3 MHz and 2.8 MHz sub-carriers. Fluorescent lighting (specifically those with T-12 ballasts) produces infrared noise that interferes with communication. Infrared receivers tend to use a wider spectrum diode with pass band filters that are more vulnerable to infrared interference.

In-Vitro Testing of Wireless Communication

The ability to communicate in a wireless manner is a key aspect of the proposed technology. The major communication methods to be explored include RF, infrared, and tissue based conduction. Each method has its weaknesses and it is likely that an integrated method for communication will be used. During Phase I, we will explore the use of all forms of light or similar such as IR and RF communication for short distances while continuing work on the software, sensing and output circuits of the breadboard prototype system.

In order to address the specific challenges associated with use of light for communication between devices implanted in a human body, we have designed a chamber to provide a suitable early stage bench testing environment for wireless communication methods of implanted systems. This system will be constructed and used to investigate the various methods of wireless communication proposed for the system.

Two chambers will be constructed: 1) cylindrical and 2) cubic form.

The primary material framework will consist of non-conducting plastic frame with outer shell consisting of interchangeable walls. The system provides for watertight seals so that it can be filled with solutions of various viscosity and light altering characteristics. In addition there is a mechanism in place to insert various optical wavelength filters along the outer surface of the chamber as well as inside the various sub-compartments. Each compartment can be individualized and the distances between walls (i.e. interface) is adjustable within the chamber. The functional chamber dimensions have been determined using CT scan images to recreate an average distance between major thoracic structures such as the sling to thoracic cage (the most variable parameter due to dependence on patient's body mass index), pleural space, mediastinal space and max/min distances on inspiration and expiration. The goals are not to create an exact replica of the human thorax, but to have a clinically relevant test chamber for testing various modes of communication.

Signal generation of light as well electromagnetic interference will be built as insertion boards throughout the chamber. Various light wavelengths including those produced by fluorescent and ambient lighting will be reproduced and evaluated for the impact on effective and reliable communication between intelligent modules.

The communication sensors and emitters can be placed within the chamber at various locations that correspond to anatomically relevant distances and angles, with the intervening space consisting of sub-compartments equipped with a combination of solutions and optical filters to mimic the interface changes between tissue layers within the body. In addition to non-biological materials being used, it also supports the capability to use actual organs and tissues (i.e. heart and lungs from a slaughterhouse pig). There is method for pumping solutions (pulsatile and non-pulsatile flow) throughout the various chambers or biologic tissue during experiments designed to test the differences in light transmission that might be seen in the chest while the lungs expand and heart beats. The contribution low frequency respiration and the slightly higher frequency of cardiac beating movement on noise generation during communication can be studied. Since temperature affects light transmission and tissue absorption characteristics, the fluid and chamber will be maintained at 37 degrees C.±10 degrees to determine the extreme of temperatures with the most variability being at the skin: subcutaneous tissue interface and minimal temperature variation at core organs such as the heart. One can predict that when the heart fills with blood or lungs fill with air, the dimensions, distances and relationship between the chest structures change. The effect of this periodic distance oscillation in the 3-dimensional environment will be explored during Phase I and studied in detail during Phase 2.

During Phase I, the chamber will provide the data needed for confirmation of wireless communication, its limits, and design considerations for the implanted version of the prototype. A number of infrared source parameters will be explored. The parameters we will investigate include:

I. Wave length: Infrared sources are available at 830 nm, 850 nm, 880 nm and 940 nm. Experiments will be designed to determine which wavelengths have optimal tissue absorption and refraction. Statistically designed experiments will identify the significance of this parameter. Student T-tests will be used to compare the response at different wavelengths.

2. Optical Power and Energy Density: Infrared sources are available at various maximum power and energy densities. Experiments will be designed to determine energy densities and total power required to overcome tissue absorption providing reliable communication in vivo.

Silicon photo detectors are available in many sizes (active areas) and packages. We will initially use a UDT Sensors, Inc. pin: S-IOCL sold in "chip" form. It is not installed in a package and thus has the largest percentage of active area relative to its dimensions.

Numerous modifications and alternative embodiments of the present invention will be apparent to those skilled in the art in view of the foregoing description. Accordingly, this description is to be construed as illustrative only and is for the purpose of teaching those skilled in the art the best mode for carrying out the present invention. Details of the structure may vary substantially without departing from the spirit of the present invention, and exclusive use of all modifications that come within the scope of the appended claims is reserved. Within this specification embodiments have been described in a way which enables a clear and concise specification to be written, but it is intended and will be appreciated that embodiments may be variously combined or separated without parting from the invention. It is intended that the present invention be limited only to the extent required by the appended claims and the applicable rules of law.

It is also to be understood that the following claims are to cover all generic and specific features of the invention described herein, and all statements of the scope of the invention which, as a matter of language, might be said to fall there between.

What is claimed is:

1. An intra-body communication system for monitoring physiological changes in a patient comprising:
    a first device implanted into a patient's body at a target site, wherein the first device comprises a cell layer having cells from the target site pre-positioned on or in the first device prior to its being implanted, wherein the pre-positioned cells are adapted to respond to a physiological signal from the patient;
    a second device spaced apart from the first device, wherein the second device is implanted into the patient's body and is capable of drug delivery;
    the first device and second device capable of engaging in a two-way communication through transmission of one or more infrared signals through at least a portion of the patient's body between the first device and the second device, wherein the one or more infrared signals travel through the body with minimal interference from a surrounding tissue or organ;
    a receiver for detecting and/or decoding the one or more infrared signals to monitor physiological changes in the patient and for triggering an adjustment in drug delivery from the second device; and
    the receiver for sending information to a physician.

2. The system of claim 1, wherein the first device further comprises an electronic component.

3. The system of claim 2, wherein the electronic component comprises at least one sensor and at least one electrode contacting said biologic component.

4. The system of claim 1, wherein the two-way communication includes transmitting and receiving infrared signals.

5. The system of claim 1, wherein the one or more infrared signals measure blood pressure, ECG, heart rate, body temperature, glucose levels, gene changes, protein changes, local cellular changes that reflect systemic disease or change in health status, or combinations thereof.

6. The system of claim 1, wherein the receiver compares the one or more infrared signals to a reference signal to diagnose a disease or condition.

7. The system of claim 1, wherein the receiver decodes the one or more infrared signals to trigger an event.

8. The system of claim 7, wherein the event includes adjusting the patient's medical treatment.

9. A method for monitoring physiological changes in a patient, the method comprising the steps of:
    providing an intra-body communication system comprising:
        a first device implanted into a patient's body at a target site, wherein the first device comprises a cell layer having cells from the target site pre-positioned on or in the first device prior to its being implanted, wherein the pre-positioned cells are adapted to respond to a physiological signal from the patient;
        a second device spaced apart from the first device, wherein the second device is implanted into the patient's body and is capable of drug delivery;
        the first device and second device capable of engaging in a two-way communication through transmission of infrared signals through at least a portion of the patient's body between the first device and the second device, wherein the wherein the infrared signals travel through the body with minimal interference from a surrounding tissue or organ; and
        a receiver for detecting and/or decoding the infrared signals to monitor physiological changes in the patient;
    transmitting the infrared signals through at least a portion of the patient's body between the first device and the second device;
    providing the receiver for detecting and/or decoding the infrared signals to monitor physiological changes in the patient and for triggering an adjustment in drug delivery from the second device; and
    the receiver for sending information to a physician.

10. A method of diagnosing a patient, the method comprising:
    providing an intra-body communication system comprising:
        a first device implanted into a patient's body at a target site, wherein the first device comprises a cell layer having cells from the target site pre-positioned on or in the first device prior to its being implanted, wherein the pre-positioned cells are adapted to respond to a physiological signal from the patient;
        a second device spaced apart from the first device, wherein the second device is implanted into the patient's body and is capable of drug delivery; and
        the first device and second device capable of engaging in a two-way communication through transmission of infrared signals through at least a portion of the patient's body between the first device and the second device, wherein the infrared signals travel through the body with minimal interference from a surrounding tissues or organs;

a receiver for detecting and/or decoding the infrared signals to monitor physiological changes in the patient;

transmitting the infrared signals through at least a portion of the patient's body between the first device and the second device;

detecting and/or decoding the infrared signals to monitor physiological changes in the patient; and comparing the infrared signals in the patient to a reference signal to diagnose a disease or condition, and in response, to adjust drug delivery from the second device; and the receiver for sending information to a physician.

11. A method of treating a patient, the method comprising:
providing an intra-body communication system comprising:
- a first device implanted into a patient's body at a target site, wherein the first device comprises a cell layer having cells from the target site pre-positioned on or in the first device prior to its being implanted, wherein the pre-positioned cells are adapted to respond to a physiological signal from the patient;
- a second device spaced apart from the first device, wherein the second device is implanted into the patient's body and is capable of drug delivery;
- the first device and second device capable of engaging in a two-way communication through transmission of infrared signals through at least a portion of the patient's body between the first device and the second device, wherein the infrared signals travel through the body with minimal interference from a surrounding tissues or organs; and
- a receiver for detecting and/or decoding the infrared signals to monitor physiological changes in the patient;

transmitting the infrared signals through at least a portion of the patient's body between the first device and the second device;

detecting and/or decoding the infrared signals to monitor physiological changes in the patient;

reviewing and/or analyzing the infrared signals;

treating the patient based on the review and/or analysis of the infrared signals and initiating an adjustment in drug delivery from the second device; and the receiver for sending information to a physician.

* * * * *